United States Patent
Daulton et al.

(10) Patent No.: US 6,322,559 B1
(45) Date of Patent: Nov. 27, 2001

(54) ELECTRODE CATHETER HAVING COIL STRUCTURE

(75) Inventors: Jay S. Daulton, San Jose; Dawn Henderson, Palo Alto, both of CA (US)

(73) Assignee: VNUS Medical Technologies, Inc., San Jose, CA (US)

( * ) Notice: Subject to any disclaimer, the term of this patent is extended or adjusted under 35 U.S.C. 154(b) by 0 days.

(21) Appl. No.: 09/110,588

(22) Filed: Jul. 6, 1998

(51) Int. Cl.$^7$ ..................................................... A61B 18/14
(52) U.S. Cl. .............................. 606/41; 607/99; 607/122; 607/113
(58) Field of Search .................................. 606/41, 47, 49, 606/50; 607/99, 122, 113; 600/374, 381, 393

(56) References Cited

U.S. PATENT DOCUMENTS

| | | |
|---|---|---|
| 164,184 | 6/1875 | Kidder . |
| 373,339 | 11/1887 | Hamilton . |
| 3,301,258 | 1/1967 | Werner et al. . |
| 3,557,794 | 1/1971 | Van Patten . |
| 4,154,246 | 5/1979 | LeVeen . |
| 4,699,147 | 10/1987 | Chilson et al. . |
| 4,709,698 | 12/1987 | Johnston et al. . |
| 4,765,331 | 8/1988 | Petruzzi et al. . |
| 4,776,349 | 10/1988 | Nashef et al. . |
| 4,966,597 | 10/1990 | Cosman . |
| 5,078,717 | 1/1992 | Parins et al. . |
| 5,078,736 * | 1/1992 | Behl ......................................... 623/1 |
| 5,117,828 | 6/1992 | Metzger et al. . |
| 5,122,137 | 6/1992 | Lennox . |
| 5,156,151 | 10/1992 | Imran . |
| 5,228,442 | 7/1993 | Imran . |
| 5,239,999 | 8/1993 | Imran . |
| 5,251,634 | 10/1993 | Weinberg . |
| 5,263,493 | 11/1993 | Avitall . |
| 5,275,610 | 1/1994 | Eberbach . |
| 5,279,299 | 1/1994 | Imran . |

(List continued on next page.)

FOREIGN PATENT DOCUMENTS

| | | |
|---|---|---|
| 0 189 329 A2 | 7/1986 | (EP) . |
| WO 95/02370 | 1/1995 | (WO) . |
| WO 95/10236 | 4/1995 | (WO) . |
| WO 95/10322 | 4/1995 | (WO) . |
| WO 95/31142 | 11/1995 | (WO) . |
| WO 97/17892 | 5/1997 | (WO) . |
| WO 97/32532 | 9/1997 | (WO) . |

OTHER PUBLICATIONS

"Electrofulguration for Varicose Veins," The Medical Letter on Drugs and Therapeutics, vol. 10, No. 14, Jul. 12, 1968, at 53–55.

Watts, "Endovenous Diathermy Destruction of Internal Saphenous," British Medical Journal, Oct. 7, 1972, p. 53.

(List continued on next page.)

*Primary Examiner*—Lee Cohen
(74) *Attorney, Agent, or Firm*—Fulwider Patton Lee & Utecht, LLP (57) ABSTRACT

A coil is located at the distal working end of an electrode catheter. The coil includes two parallel electrically conductive strips separated by a narrow gap. The strips are covered with insulation, and are connected respectively to electrical leads having opposite polarity. Electrodes are formed by removing portions of the insulation from the strips. The coil can be expanded to define an increased effective diameter at the working end of the catheter. An RF field produced along the helical path defined by the strips of the coil is unaffected by the expanded state of the coil. The energy from the RF field heats the surrounding venous tissue and causes a reduction in the diameter of the vein. The expanded coil mechanically prevents the vein from shrinking beyond the effective diameter defined by the expanded coil and the patency of the vein is maintained for venous function.

64 Claims, 9 Drawing Sheets

U.S. PATENT DOCUMENTS

| | | |
|---|---|---|
| 5,293,869 | 3/1994 | Edwards et al. . |
| 5,304,120 | 4/1994 | Crandell et al. . |
| 5,311,866 * | 5/1994 | Kagan et al. ................ 600/374 |
| 5,318,564 | 6/1994 | Eggers . |
| 5,387,233 | 2/1995 | Alferness et al. . |
| 5,397,339 | 3/1995 | Desai . |
| 5,404,638 | 4/1995 | Imran . |
| 5,405,322 | 4/1995 | Lennox et al. . |
| 5,406,946 | 4/1995 | Imran . |
| 5,411,025 | 5/1995 | Webster, Jr. . |
| 5,411,546 | 5/1995 | Bowald et al. . |
| 5,431,649 * | 7/1995 | Mulier et al. ................ 606/41 |
| 5,437,664 | 8/1995 | Cohen et al. . |
| 5,441,516 | 8/1995 | Wang et al. . |
| 5,449,381 | 9/1995 | Imran . |
| 5,458,596 | 10/1995 | Lax et al. . |
| 5,462,545 | 10/1995 | Wang et al. . |
| 5,465,717 | 11/1995 | Imran et al. . |
| 5,514,130 | 5/1996 | Baker . |
| 5,549,108 * | 8/1996 | Edwards et al. ................ 128/642 |
| 5,709,224 | 1/1998 | Behl et al. . |
| 5,722,401 * | 3/1998 | Pietroski et al. ................ 128/642 |
| 5,725,525 * | 3/1998 | Kordis ................ 606/41 |
| 5,810,802 * | 9/1998 | Panescu et al. ................ 606/31 |
| 5,827,268 | 10/1998 | Laufer . |
| 5,853,411 * | 12/1998 | Whayne et al. ................ 606/41 |
| 5,863,290 | 1/1999 | Gough et al. . |
| 5,871,531 * | 2/1999 | Struble ................ 607/126 |
| 5,972,026 * | 3/2000 | Laufer et al. ................ 607/96 |
| 6,004,316 * | 12/1999 | Laufer ................ 606/28 |
| 6,033,397 * | 3/2000 | Laufer et al. ................ 606/27 |
| 6,033,398 * | 3/2000 | Farley et al. ................ 606/27 |
| 6,036,687 * | 3/2000 | Laufer et al. ................ 606/27 |

OTHER PUBLICATIONS

O'Reilly, "Endovenous Diathermy Sclerosis as a Unit of the Armamentarium for the Attack on Varicose Veins," The Medical Journal of Australia, Jun. 1, 1974, at 900.

O'Reilly, "Endovenous Diathermy Sclerosis of Varicose Veins," Aust. N.Z. J. Surg., vol. 47, No. 3, Jun. 1977, pp. 393–395.

Brunelle, et al., "A Bipolar Electrode for Vascular Electrocoagulation with Alternating Current," Technical Notes, Oct. 1980, at 239–240.

O'Reilly, "A Technique of Diathermy Sclerosis of Varicose Veins," Aust. N.Z. J. Surg., vol. 51, No. 4, Aug. 1981, pp. 379–382.

Cragg et al., "Endovascular Diathermic Vessel Occlusion," Diagnostic Radiology, 144: 303–308, Jul. 1982.

Money, "Endovascular Electroablation of Peripheral Veins," 22nd Annual Symposium, Current Critical Problems, New Horizons and Techniques in Vascular and Endovascular Surgery (Nov. 1995).

Crockett, et al., "Preliminary Experience with an Endovascular Catheter for Electrocoagulation of Peripheral Veins," The Journal of Vascular Technology, Winter 1996, at 19–22.

* cited by examiner

ELECTRODE CATHETER HAVING COIL STRUCTURE

BACKGROUND OF THE INVENTION

This invention relates to a catheter-based system to position an electrode for providing energy to a biological site, and more particularly, to a catheter having an expandable distal end configured to maintain a desired spacing between bipolar electrodes.

The venous system of the lower limb consists essentially of the superficial venous system and the deep venous system with perforating veins connecting the two systems. The superficial system includes the long or great saphenous vein and the short saphenous vein. The deep venous system includes the anterior and posterior tibial veins which unite to form the popliteal vein, which in turn becomes the femoral vein when joined by the short saphenous vein.

Veins are hollow anatomical structures which contain numerous one-way valves for directing blood flow back to the heart. The venous valves prevenrograde flow as blood is pushed forward through the vein lumen and back to the heart. Each cusp of bicuspid venous valves form a sack or reservoir for blood which, under pressure, forces the free surfaces of the cusps together to prevent retrograde flow of the blood and allow antegrade flow to the heart. When an incompetent valve is in the flow path of retrograde flow toward the foot, the valve is unable to close because the cusps do not form a proper seal and retrograde flow of blood cannot be stopped.

Incompetent valves in the venous system can occur with vein dilation. Separation of the cusps of the venous valve at the commissure may occur as a result. The leaflets are stretched by the dilation of the vein and concomitant increase in the vein diameter which the leaflets traverse. Stretching of the leaflets of the venous valve allows the loose leaflets to fold on themselves and leave the valve open. This prolapse can allow reflux of blood in the vein. Eventually the venous valve fails, thereby increasing the pressure on the lower venous sections and overlying tissues. Two venous diseases which often involve vein dilation are varicose veins and chronic venous insufficiency.

The varicose vein condition includes dilation of the veins of the lower limb, resulting in unsightly discoloration, pain and ulceration. Varicose veins often involve incompetence of one or more venous valves, which allow reflux of blood from the deep venous system to the superficial venous system or reflux within the superficial system. Current treatments include such invasive open surgical procedures as vein stripping, sclerotherapy, and occasionally, vein grafting, venous valvuloplasty, and the implantation of various prosthetic devices. The removal of varicose veins from the body can be a tedious, time-consuming procedure having a painful and slow healing process. Complications, scarring, and the loss of the vein for future cardiac and other by-pass procedures may also result. Along with the complications and risks of invasive open surgery, varicose veins may persist or reoccur, particularly when the valvular problem is not corrected. Due to the long and tedious nature of the surgical procedure, treating multiple venous sections can exceed the physical stamina of the physician, and thus render complete treatment of the varicose vein conditions impractical.

As the veins dilate due to increased pressure, the valves in the veins fail. This causes the pressure to increase on the next valve and vein segment down, causing those veins to dilate, and as this continues, the valves in the veins eventually all fail. As they fail, the effective height of the column of blood above the feet and ankles grows, and the weight and hydrostatic pressure increases. When the weight of that column reaches a critical point from the valve failures, ulcerations of the ankle begin to form. These ulcerations do not heal easily because the weight of blood which caused them continues to persist.

The ligation of vascular lumen by cauterization or coagulation using electrical energy from an electrode has been employed as an alternative to the surgical removal of such veins. However, ligation procedures close off the lumen, essentially destroying their functional capability. For example, it is known to introduce an electrode into the leg of a patient, and position the electrode adjacent the exterior of the varicose veins to be treated. Through a small stab incision, a probe is forced through the subcutaneous layer between the fascia and the skin, and then to the various veins to be destroyed. Electrodes at the outer end of the probe are placed adjacent the varicose veins. Once properly positioned, an alternating current of about 500 kilohertz is applied to destroy the adjacent varicose veins. Such veins are no longer capable of allowing blood to flow through, and are no longer of use. For example, ligating the saphenous vein would render that vein unavailable for harvesting in other surgical procedures such as coronary by-pass operations. Ligation techniques which functionally destroy the vein lumen would appear be inappropriate to a corrective procedure for restoring and maintaining the function of the vein.

Electrode catheters having longitudinal arms circumferentially spaced on the catheter, with electrodes of opposite polarity being located on adjacent arms, can produce an RF field around the . The longitudinal arms can be expanded away from the catheter. As the longitudinal arms are expanded radially away from the catheter, the space between the electrodes on the arms increase. RF field would be,weaker as the longitudinal arms are expanded away from the catheter, and stronger as the arms are brought closer to the catheter. Thus, the heating effect from the field generated by the electrodes would vary during the procedure. A more constant field generated during the procedure should allow for a more predicable heating effect.

Hence, those skilled in the art have recognized a need for an expandable catheter system that maintains the same bipolar electrode spacing regardless of the degree of expansion of the catheter for a more predictable heating effect. Those skilled in the art also recognize a need for a less expensive expandable catheter in addition to one that can be more easily manufactured.

SUMMARY OF THE INVENTION

Briefly, and in general terms, the present invention provides a less invasive and faster method for solving the underlying problems of varicose veins and venous insufficiency, and uses a novel repair system, including a catheter for placement of electrodes for delivering energy. The present invention includes a method of applying energy to cause shrinkage of a vein, the method comprising the steps of introducing a catheter into the hollow anatomical structure, the catheter having a coiled member, expanding a coil to place a heating device in apposition with the wall of the hollow anatomical structure, applying energy from the heating device to heat the wall of the hollow anatomical structure and cause the hollow anatomical structure to durably assume a reduced diameter, and preventing shrinkage beyond the reduced diameter so that the hollow anatomical structure remains patent.

An apparatus for causing shrinkage of a hollow anatomical structure comprises a catheter having a working end, means for heating a venous treatment area to cause shrinkage of the hollow anatomical structure, wherein the means for heating is located at the working end of the catheter, and a coil expanded from the catheter to control the outer diameter of the heating means and limit the amount of the diameter of the hollow anatomical structure is reduced, so that the hollow anatomical structure remains patent. The heating means may include RF electrodes to heat and reduce the diameter of the hollow anatomical structure in the body.

One aspect of the present invention is that, where the hollow anatomical structure is a vein, venous valvular competency is restored by controllably reducing the diameter of the otherwise dilated lumen adjacent or at the valve of the vein to a desired diameter.

Another aspect of the present invention is that a coil member located adjacent the working end of the catheter is expanded to increase the effective diameter of the catheter and is robust enough to prevent any reduction in the diameter of the vein.

Another aspect of the present invention is that the spacing of adjacent bipolar electrodes is not altered by the expansion of the catheter so that a consistent RF field for consistent heating and heat distribution results at all diameters defined by the coil.

Yet another aspect of the present invention is that an RF field is produced along a helical path as defined by the strips of the expandable coil.

Another aspect of the present invention is that the coil can be expanded and acts as a mechanical limiter or stent so as to prevent shrinkage of the vein lumen beyond the diameter defined by the expanded coil.

Yet another aspect of the present invention is that a balloon can be inflated between the coil and the catheter shaft to occlude the vein. The inflated balloon further separates the electrodes from the surrounding blood, and reduces or prevents the formation of thrombosis. The balloon can act as a mechanical limiter to control the amount of shrinkage of the vein lumen during the application of energy from the coiled electrode.

An additional aspect of the present invention is that a seal at the distal end of the catheter prevents fluids from seeping back into the catheter.

A further aspect of the present invention is that the coil includes two parallel electrically conductive strips separated by an insulating gap in which a temperature sensor is located. The insulating gap remains uniform as the coil is expanded to define a larger effective diameter, so that a consistent RF field is produced along the coil, resulting in consistent heat distribution.

Yet a further aspect of the present invention is that the coil includes conductive strips substantially covered by an insulating film, except for portions which are to come into apposition with the venous tissue.

These and other aspects and advantages of the present invention will become apparent from the following more detailed description, when taken in conjunction with the accompanying drawings which illustrate, by way of example, the principles of the invention.

DETAILED DESCRIPTION OF THE EMBODIMENTS

As shown in the exemplary drawings, the embodiments are directed toward the intravenous treatment of veins using an electrode catheter at a venous treatment site.

As used herein, like reference numerals will designate similar elements in the various embodiments of the present invention to be discussed. In addition, unless otherwise noted, the term "working end" will refer to the direction toward the treatment site in the patient, and the term "connecting" end will refer to the direction away from the treatment site in the patient.

Figures 1, 2:
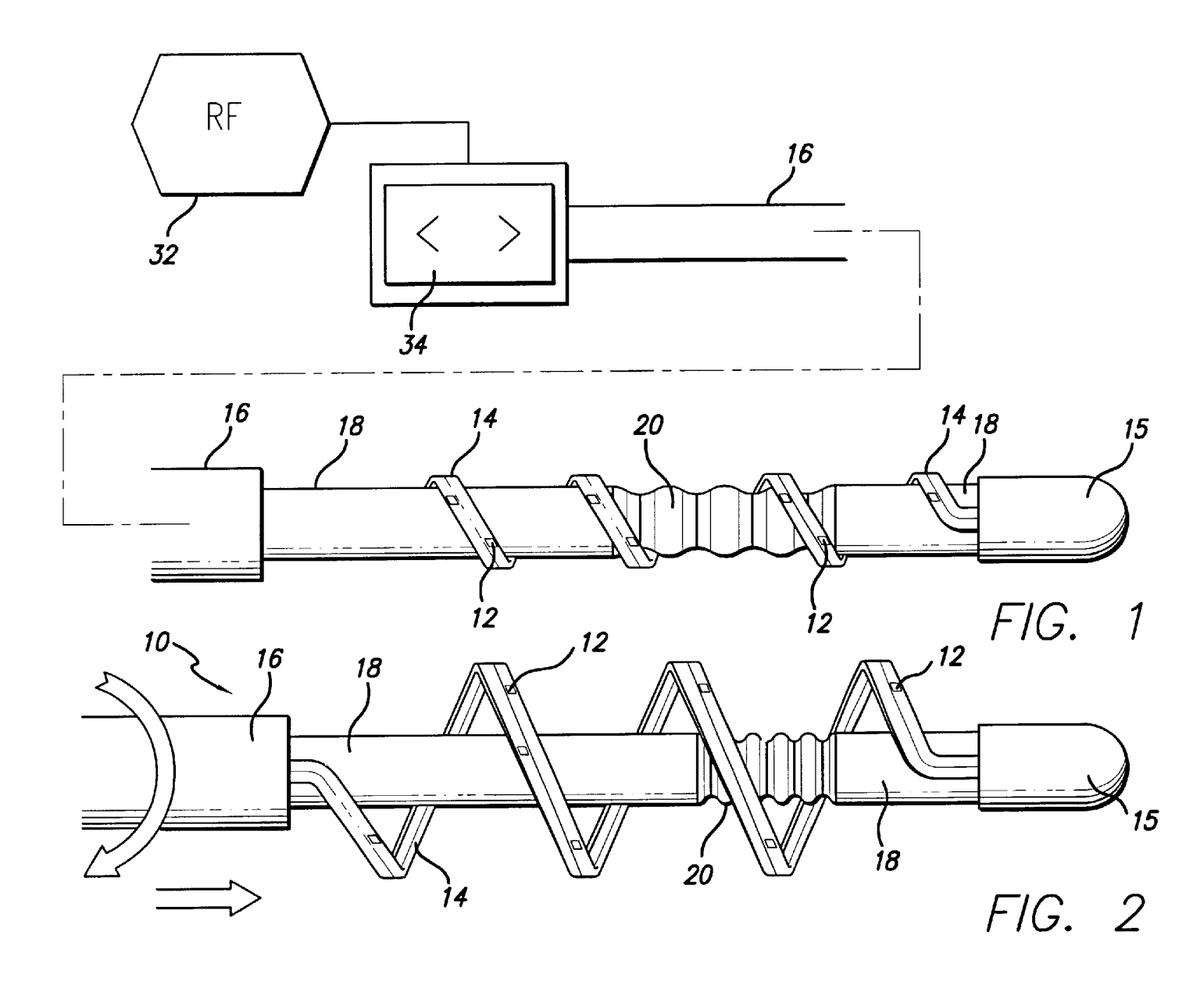
FIG. 1 shows a side view of an electrode catheter having a helical coil containing multiple electrodes in accordance with the present invention.
FIG. 2 shows the electrode catheter of FIG. 1 having a coil in an expanded configuration in accordance with the present invention.

Referring now to FIGS. 1 and 2, a minimally invasive treatment of venous insufficiency can be performed using a catheter 10 to deliver electrodes 12 to a venous treatment site in order to restore the competency of a vein. The catheter would be suitably sized for the vein to be treated. For example, a 7 French size, which has about a 2.3 millimeter (mm) diameter, can be used in the larger veins of the leg.

The working end of the catheter 10 includes electrodes 12 on a helical coil 14 to heat the surrounding venous tissue and effect shrinkage of the vein. The coil 14 is attached at one end to a tip 15 of the catheter and at the other end to a sleeve 16 of the catheter. The electrodes 12 are preferably operated as bipolar electrodes. The RF generator 32 and the electrodes 12 create an RF field around the effective diameter of the catheter as defined by the coil 14. The venous tissue is in apposition with the electrodes, and the vein becomes heated and begins to shrink.

The sleeve 16 is sufficiently stiff or rigid so as to move the coil when the sleeve is moved, and can be formed from a polymer such as polyimide. The sleeve extends down the length of the catheter to allow the physician to mechanically control the effective diameter of the working end of the catheter during the application of RF energy. The coil 14 is retracted toward the catheter when the sleeve 16 is moved away from the tip 15 at the working end of the catheter. The coil 14 is expanded away from the catheter when the sleeve 16 is moved toward the tip 15 at the working end of the catheter.

The sleeve can be connected to an actuation mechanism 34 such as a threaded control knob, or any other suitable mechanism, to provide fine control over the movement of the sleeve. The threaded knob pushes the sleeve forward as the knob is rotated in one direction. Alternately, a threaded actuation rod running down the center of the catheter could be used to move the tip toward the sleeve. The actuation mechanism preferably imparts both rotary and linear motion to the sleeve, is shown by the arrows in FIG. 2, to expand or contract the coil. Rotational movement can be introduced by threads where the sleeve connects with the actuation mechanism when the sleeve is moved forward. Rotational movement can compensate for torquing or deformation as the coil is expanded outward so as to define a substantially cylindrical shape. The use of both rotational and axial movement allows for a compact contracted coil assembly around the catheter before expansion.

By adjusting the effective diameter of the catheter defined by the coil, contact between the electrodes 12 and the vein wall can be maintained, and vein lumina having different diameters can be treated. Although the shape defined by the expandable coil 14 is substantially cylindrical, the cross-sectional diameter of the substantially cylindrical shape may not necessarily be uniform. The cross-sectional diameter may increase or decrease slightly over the length of the substantially cylindrical shape. The coil 14, however, should substantially conform to the vein lumen during treatment. The coil has sufficient structural strength when expanded to physically prevent shrinkage of a vein beyond a selected diameter so that the vein remains patent or open, where venous function or valvular competency is restored.

The coil 14 moves the electrodes 12 away from the catheter shaft and into apposition with the vein wall. The electrodes are preferably positioned on the coil such that when the coil is extended to define the reduced diameter of the vein, all of the electrodes are in apposition with the venous tissue of the vein wall. The heating effect is then focused into the vein wall. The coil can have any suitable length to treat a vein, including an extended venous section such as an esophageal varix. The insulated surfaces of the coil are exposed to the blood or other fluid in the lumen being treated. The uninsulated conductive surfaces of the coil act as electrodes and are exposed to the lumen. The energy from the electrodes is preferably directed into the wall of the lumen to prevent heating of the blood or other fluid.

Safety stops 18 are preferably formed on both the tip 15 and the sleeve 16. The stops prevent the tip and sleeve from moving too close to one another. A cover 20 can be attached to either the stops or the tip and sleeve. The cover acts as a seal and prevents blood or other fluids from flowing or seeping back between the sleeve and the remainder of the catheter. The cover 20 preferably comprises a bellow or pleats which allows the cover to fold into a compact configuration when the tip and sleeve are moved toward one another.

The cover can be manufactured from a flexible elastomeric polymer such as low density polyethylene. A tension rod (not shown) extending down the catheter from the tip resists elongation or stretching of the length of the catheter that might otherwise be caused by longitudinal movement of the sleeve 16 and assists in maintaining the position of the tip when the sleeve is moved to adjust the effective diameter defined by the coil.

The catheter further includes a guide wire lumen for accepting a guide wire (not shown). The guide wire lumen is preferably insulated so as to prevent or minimize any coupling effect the electrodes may have on the guide wire. The guide wire can be removed before the application of RE energy to the electrodes. The guide wire lumen can also allow for the delivery or perfusion of medicant and cooling solution to the treatment area during application of the RF energy. It is to be understood that a guide wire may not be required for embodiments to be used for treating smaller veins.

Figure 3:
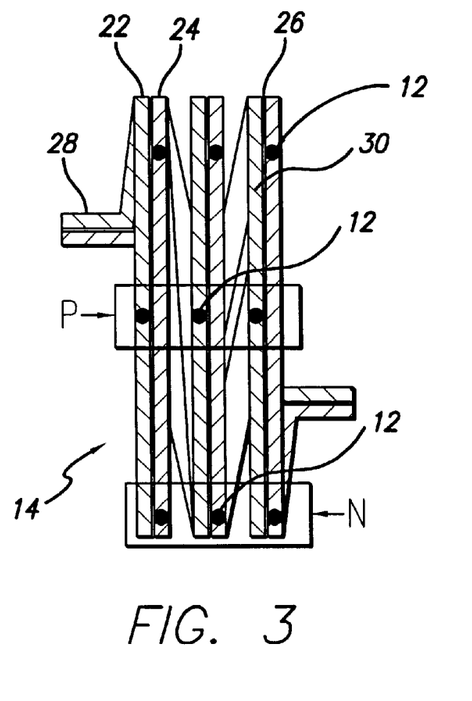
FIG. 3 shows a side view of a coil usable in the catheter of FIG. 1, having electrodes in accordance with the present invention.
Figure 4:
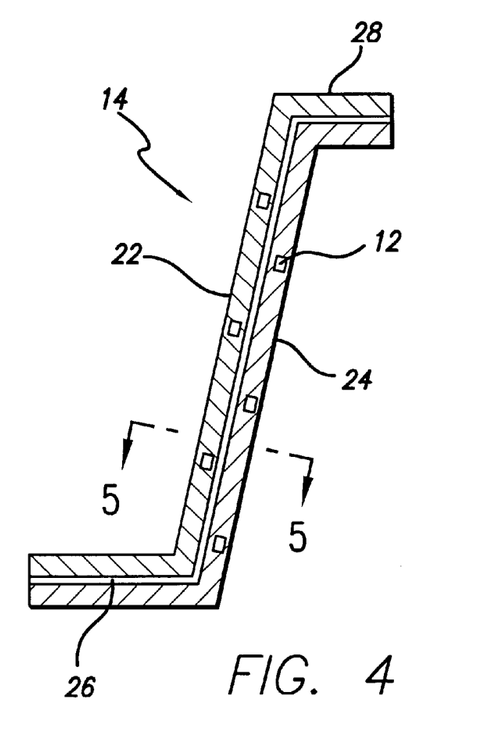
FIG. 4 shows a view of two strips before forming a coil in accordance with the present invention.

As illustrated in FIGS. 3 and 4, the coil 14 includes two insulated strips of conductive material 22 and 24. The first strip 22 is connected to a lead having one polarity, and the second strip 24 is connected to a lead having another polarity. For example, the first strip may have a positive polarity, and the second strip may have a negative polarity.

The leads to the first and second strips are connected to an RF generator. The RF generator is activated to provide suitable RF energy to the electrodes, preferably at a low power level, and preferably at a selected frequency from a range of 250 kHz to 350 MHZ. For example, one suitable frequency is 510 kHz. One criterion for the selection of the applied frequency is to minimize capacitance and power losses in the electrode leads. Another criterion is compatibility with filter circuits which can be used to eliminate RF noise from thermocouple signals.

The strips 22 and 24 have an elongated shape and may be fabricated from stainless steel, spring steel, or nitinol, or any other suitable material. When uncoiled, the strips can have a shape which resembles the letter Z. The strips can have any suitable dimension for the vein, lumen or other anatomical structure being treated. For example, the strips can have dimensions of about 0.005 inches by 0.04 inches (about 0.12 mm by 1.0 mm), but can be larger or smaller, as required for the particular lumen or structure being treated. The strips could be biased to return to a reduced diameter profile. The strips 22 and 24 are separated by a gap 26 which facilitates insulating the first and second strips from one another. The strips include tangs 28 on each end which are to be attached to the tip and sleeve of the catheter. The majority of the surface area of the strips is covered with insulation 30, which along with the gap 26, electrically insulates the conductive strips from one another. The back of the strips is insulated to prevent any unintended heating effects on the blood flowing through the vein. The insulation can be composed of polyimide film or another suitable insulating material. The insulation 30 is removed in certain areas to form the electrodes 12. The insulation 30 preferably covers the peripheral edges of the exposed face of the strips to isolate the blood flow from unintended heating effects. As illustrated in FIG. 3, electrodes 12 formed on the first strip 22 have one polarity (P), and electrodes 12 formed on the second strip 24 have a second polarity (N). The electrodes are separated by a constant distance along the coil.

The exposed areas forming the electrodes are preferably the areas which directly contact the vein wall during apposition. The electrodes are preferably positioned and formed on the coil such that all of the electrodes are in apposition with the vein wall during treatment. When the coil 14 is fully expanded, such as where the stops 18 prevent further movement between the sleeve 16 and tip 15, all of the electrodes 12 are preferably in apposition with the vein wall.

The larger the exposed surface of the electrodes apposed against the vein wall during shrinkage, the greater the surface area of the vein wall affected by the field generated by the electrodes. The heating effect is greatest when the electrodes are close together and the electrical field density or power density is greatest. Shrinkage of the vein would be concentrated where the RF field was strongest. Where electrodes are carried on the midsection of longitudinal members which bow outwardly from the catheter during expansion, the spacing between the electrodes increases during expansion and decreases during retraction. The field density can dramatically increase as the bowed members are retracted toward the catheter which brings the electrodes on the adjacent members closer together. The distance between the electrode loops of the coil formed along the longitudinal axis of the catheter can be maintained fairly constant by controlling the relative axial and rotary movement of the actuation sleeve. Although the distance between the electrode loops formed along the longitudinal axis of the catheter may change as the coil unfolds, the electrodes 12 on the coil 14 remain a constant distance apart along the path defined by the coil regardless of expansion or retraction. The density of the RF field along the path of the coil remains substantially constant.

Figure 5:
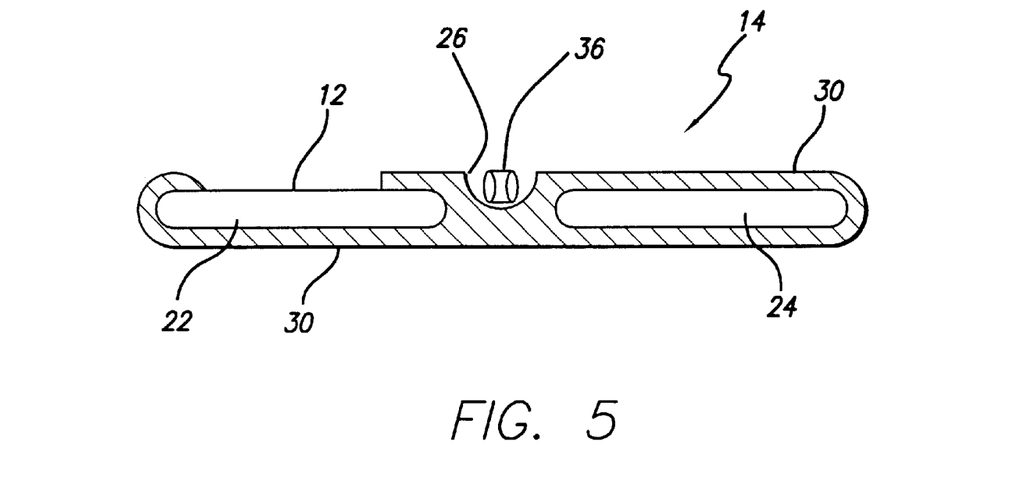
FIG. 5 shows a cross-sectional view of the coil along lines 5—5 in FIG. 4 in accordance with the present invention.

As illustrated in FIG. 5, a temperature sensor such as a thermocouple 36 can be located in the insulation 30 at the gap 26 near where one of the electrodes 12 is located to measure the temperature at a treatment site. The thermocouple can sense the temperature of the vein wall where RF energy is being applied by the electrode. The thermocouple can monitor the temperature of the treatment site to provide feedback control for application of the RF energy to control the vein wall temperature. The thermocouple can be used with an automated system to shut down the application of RF energy from the electrodes to the venous section when sufficient shrinkage of the vein is detected and to avoid overheating or cauterization of the vein.

The thermocouple 36 is preferably sized to occupy the insulated gap of the coil. One suitable dimension for the thermocouple is a 0.002 inch (about 0.05 mm) diameter, which could occupy an insulated gap of about 0.006 inches (about 0.15 mm) between the strips. The leads (not shown) to the thermocouple can be located on the side of the coil opposite the exposed electrode areas, or be formed within the insulation of the gap.

Figure 6A:
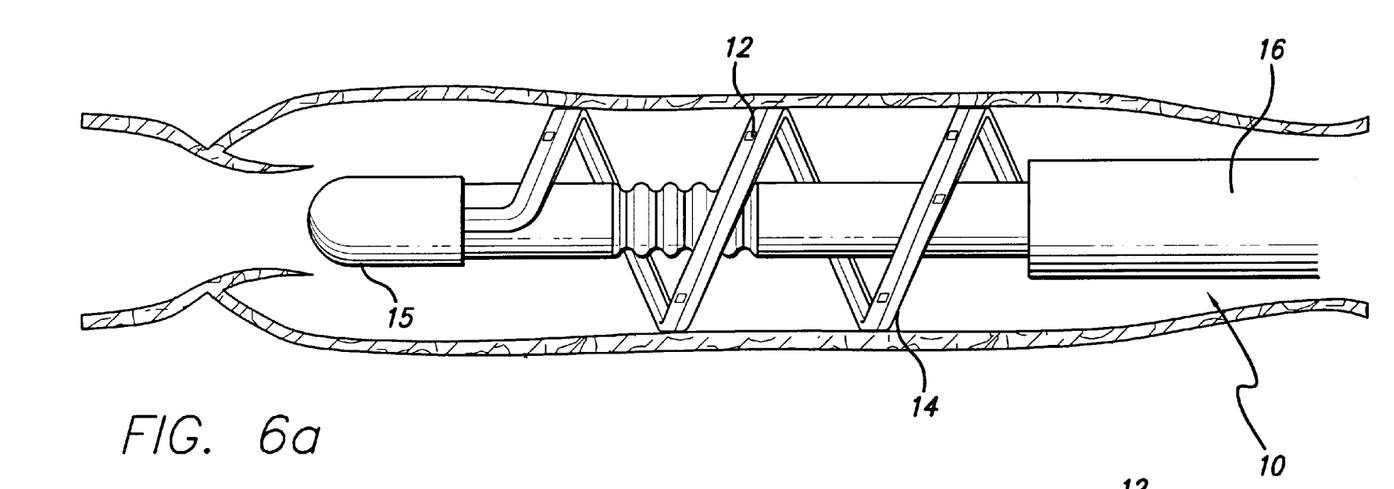
FIGS. 6a and 6b show a cross-sectional view of a venous section with a side view of a catheter in an expanded configuration with electrodes in apposition to the vein wall to deliver energy in accordance with the present invention.
Figure 6B:
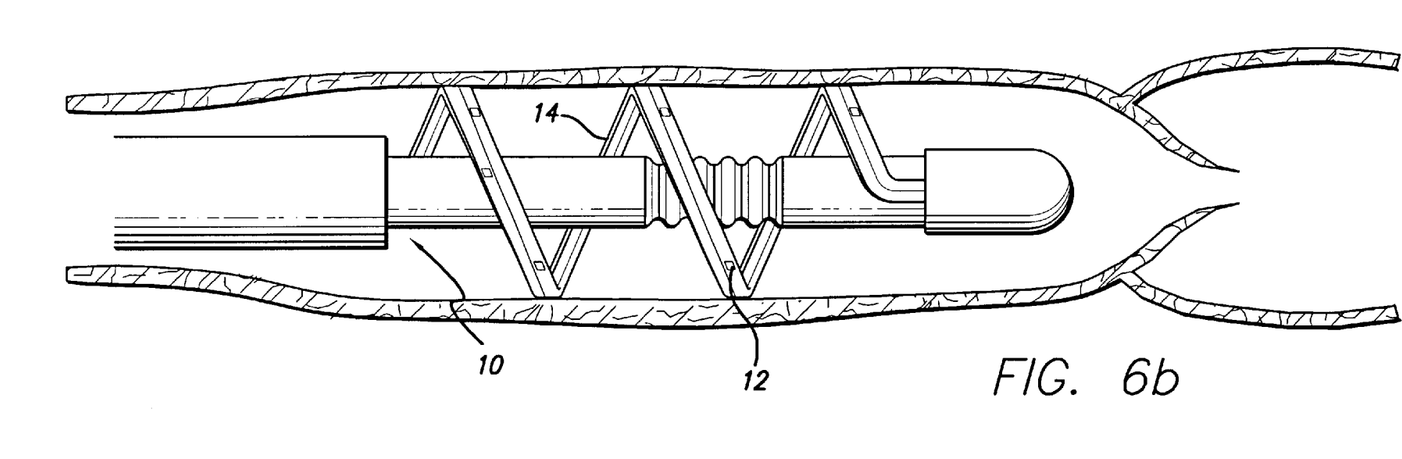

As illustrated in FIGS. 6a and 6b, after the catheter 10 is introduced and delivered to the treatment site within a dilated vein, the coil 14 is expanded to place the electrodes 12 in apposition with the vein wall. The valve within such a dilated vein is rendered incompetent where the cusps of the venous valve have separated and prolapsed. The catheter can be delivered in either an antegrade or retrograde manner. FIG. 6a illustrates the catheter 10 from a retrograde approach, and FIG. 6b illustrates the catheter from an antegrade approach. The electrodes are positioned on the coil such that the electrodes are in apposition with the vein wall during treatment. RF energy is applied by the electrodes 12 to shrink the vein. The energy emitted from the electrodes is converted within the venous tissue into heat. As the temperature of the venous tissue increases, the venous tissue begins to shrink. Substantial shrinkage can be achieved very rapidly, depending upon the specific treatment conditions, including the size of the vein being treated and power level of the applied RF energy. The shrinkage may be due in part to dehydration and the structural transfiguration of the collagen fibers in the vein. Although the collagen becomes compacted during this process, the vessel with collagen still retains elasticity. Thickening of the vein may occur during treatment which may reduce the likelihood of the recurrence of vein dilation.

The extent of shrinkage is controlled by the effective diameter of the catheter and the electrode combination. The effective diameter is defined by the coil 14. Although the coil can have some flexibility, the coil must have sufficient structural strength to prevent further shrinkage of the vein so that the vein remains patent to allow venous function. The coil 14 can be gradually retracted towards the catheter 10 during the application of RF energy, and the electrodes remain in apposition with the vein wall. The extent of vein shrinkage is monitored by fluoroscopy, ultrasound, or another suitable method. The retraction of the coil 14 is ceased when the desired reduced diameter, as defined by the effective diameter of the coil and catheter, is reached for the vein. RF energy is applied for a period of time to durably shrink the vein to the reduced diameter.

Figure 7A:
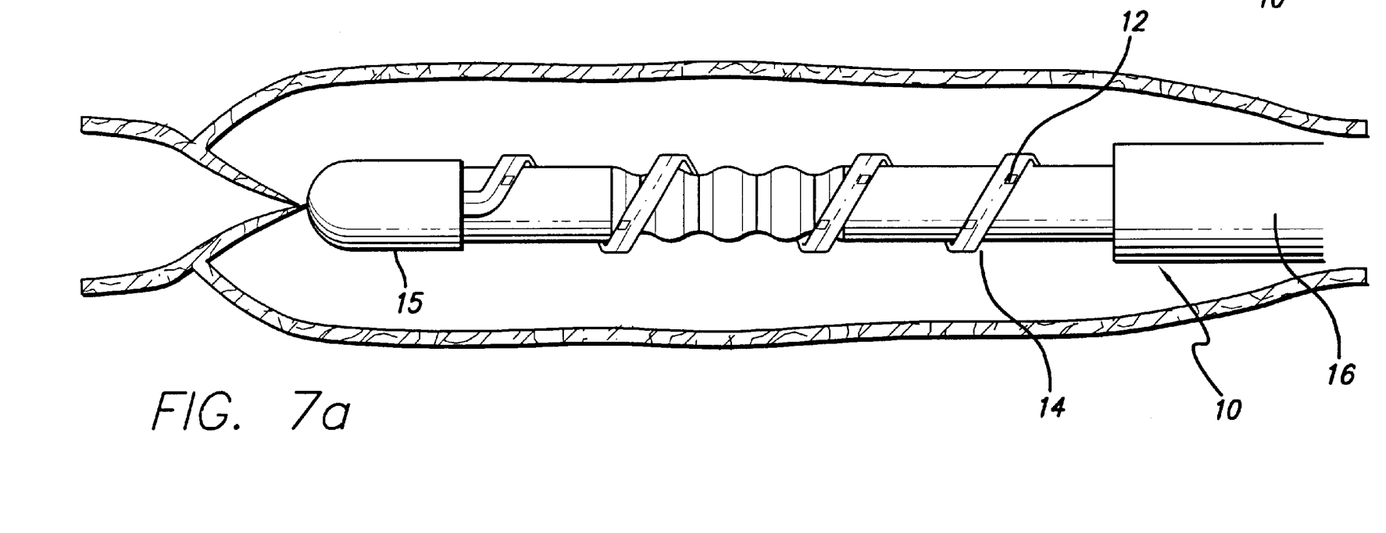
FIGS. 7a and 7b show a partial cross-sectional view of the venous section of FIGS. 6a and 6b after being treated in accordance with the present invention.
Figure 7B:
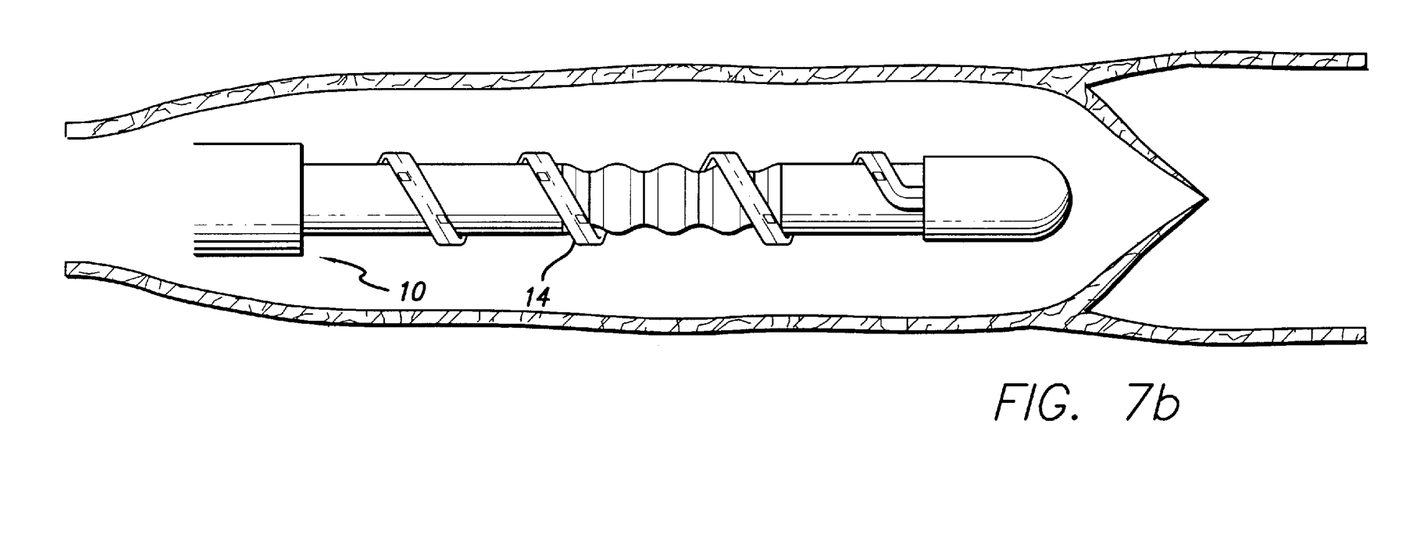

The application of RF energy is terminated, and, as illustrated in FIGS. 7a and 7b, the coil is fully retracted towards the catheter for removal. The vein, which remains patent, has been permanently reduced in diameter to restore venous function and render the venous valve competent by bringing the cusps of the valve closer together.

Figure 8:
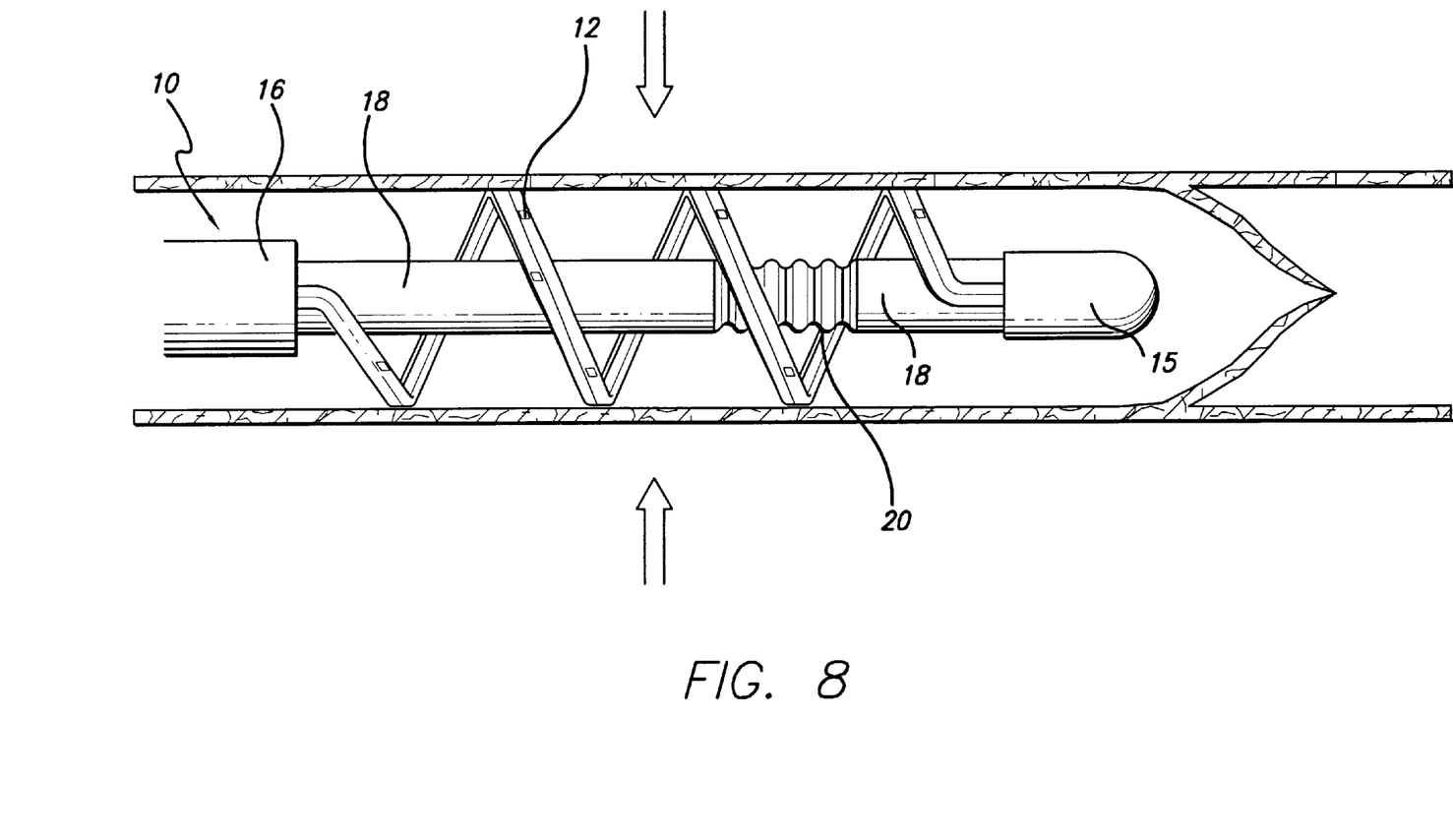
FIG. 8 is a partial cross-sectional view of a vein under external compression by a pressure cuff and which is to be treated with an electrode catheter in accordance with the present invention.

Instead of manually reducing the effective diameter of the catheter in apposition with the vein during treatment by retracting the coil until the desired reduced diameter for the vein is reached, an external pressure cuff can be applied around the limb or other anatomical structure containing the dilated vein. The pressure cuff applies pressure to the limb to compress the tissue surrounding the vein to temporarily reduce the diameter of the vein before the application of RF energy. This is illustrated in FIG. 8 by the arrows directed inward at the vein. Pressure is applied by the cuff to compress the limb until the diameter of the vein is adequately reduced to the point where venous function and valvular competency is restored. This condition can be recognized when reflux is no longer detected in the vein. Fluoroscopy, or an ultrasound transducer placed against an ultrasound window, can be used to measure the diameter or other parameters of the vein.

The catheter is delivered into the dilated venous section which may include an incompetent valve which has been compressed by the external cuff. As illustrated by FIG. 8, the electrodes 12 are then placed in apposition with the vein wall by the coil 14. The application of RF energy from the electrodes causes the vein to become heated and the vein is molded to the diameter defined by the coil. The vein would begin to shrink further but for the mechanically expanded coil defining the effective diameter of the catheter. By heating the compressed vein, the vein is effectively shrunken to the reduced diameter of the compressed vein so that when the compression by the pressure cuff is released, the vein remains in its reduced diameter condition. For example, energy can be applied by the electrodes to the compressed vein for a predetermined period of time, such as thirty or ninety seconds, while monitoring the impedance to avoid coagulation and cauterization of the vein, so that the vein durably remains at the reduced diameter for proper venous function. The coil need not be moved during the heating process. The final diameter of the treated vein was predetermined by the external pressure cuff and maintained by the stenting coil during treatment.

Figure 9:
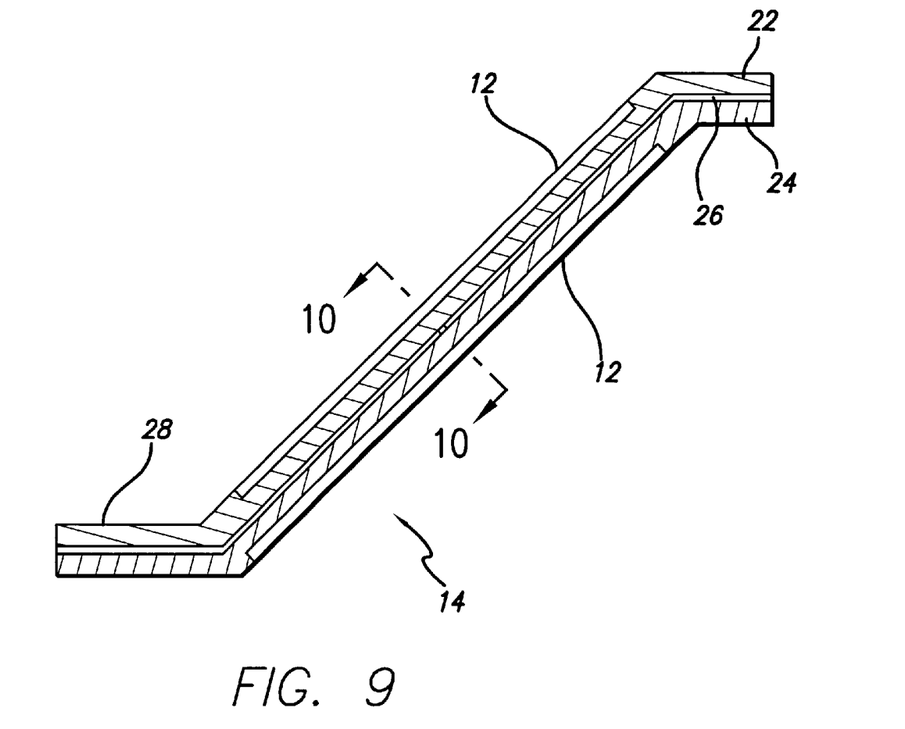
FIG. 9 shows a view of another embodiment of two strips before forming a coil in accordance with the present invention.
Figure 10:
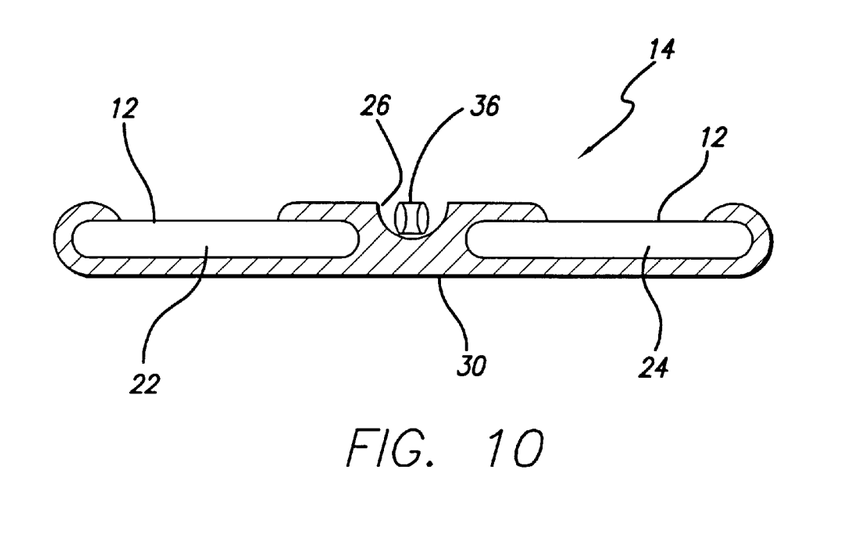
FIG. 10 shows a cross-sectional view of the coil along lines 10—10 in FIG. 9 in accordance with the present invention.

In another embodiment of the coil illustrated in FIGS. 9 and 10, a single electrode 12 is formed on each strip 22 and 24 for a substantial length along the coil. The surface area of the electrodes should be sufficient to meet the impedance requirement to effectively impart RF energy to the surrounding tissue. The larger the exposed surface of the electrodes apposed against the vein wall during shrinkage, the greater the surface area of the vein wall affected by the field generated by the electrodes. Instead of multiple alternating point electrodes, a single elongated electrode is formed on each strip of the coil. The electrode formed on the first strip 22 is connected to a lead having a polarity opposite to the polarity of the lead connected to the electrode formed on the second strip 24. A uniform RF field is produced between the electrodes along the path defined by the exposed portions of the coil which act as the electrodes.

The electrodes 12 preferably extend along the coil 14 only so far as the electrodes would be in apposition with the vein wall when the coil is fully expanded to define its maximum diameter, such as when the stops 18 prevent further relative movement between the sleeve 16 and the tip 15 of the catheter. During the application of RF energy for treatment, the electrodes should be in apposition with the vein wall, and any heating effect on the surrounding blood in the vein should be minimized.

As illustrated in FIG. 10, a temperature sensor such as a thermocouple 36 can be located in the insulation 30 at the gap 26 between the electrodes 12 to measure the temperature at a treatment site. The thermocouple senses the temperature of the vein wall where RF energy is being applied by the electrodes. The insulation 30 preferably covers the back of the coil and the peripheral edges of the exposed electrode face of the strips 22 and 24 to isolate the blood flow from unintended heating effects.

Figure 11:
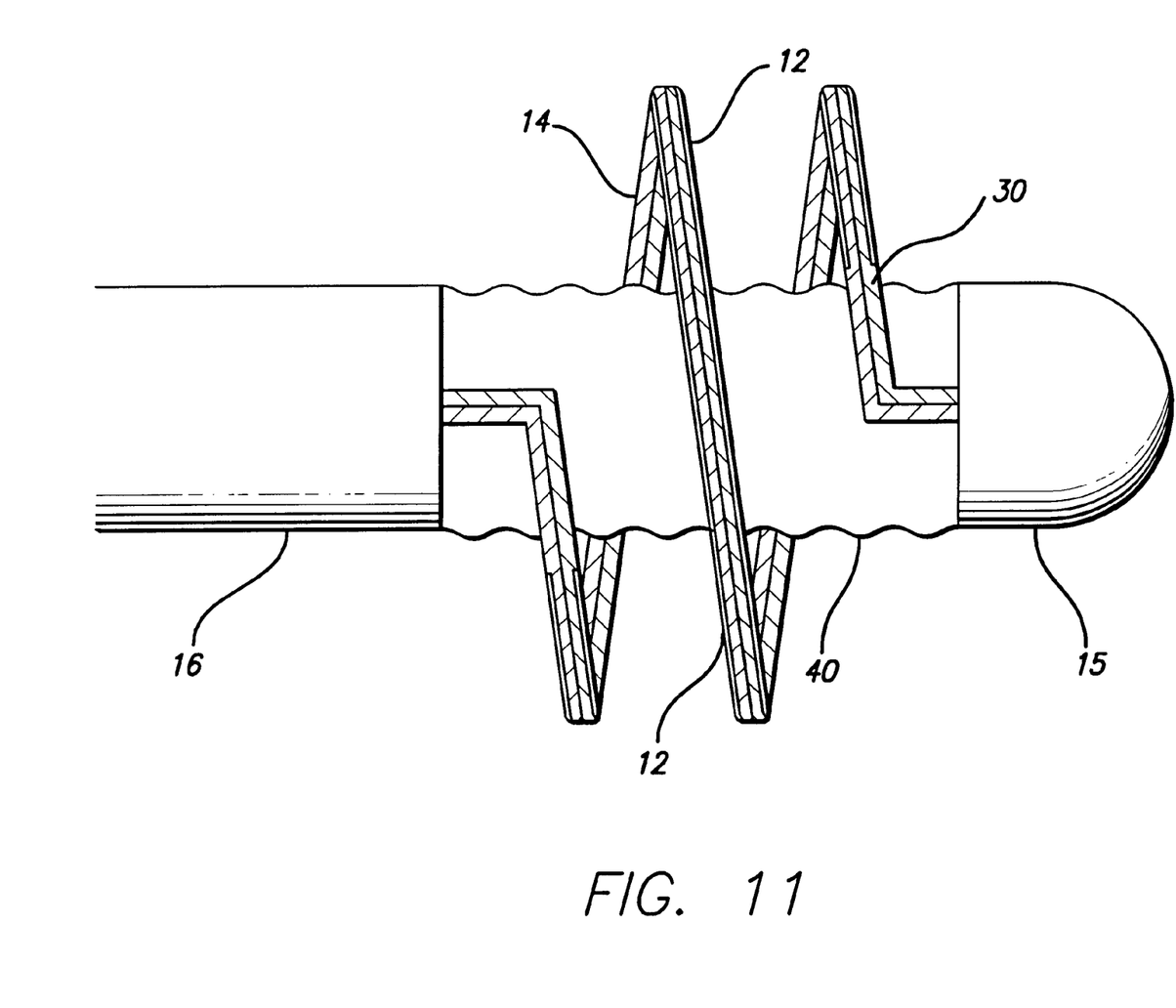
FIG. 11 shows a side view of another embodiment of the catheter having a helical coil containing electrodes in accordance with the invention.
Figure 12:
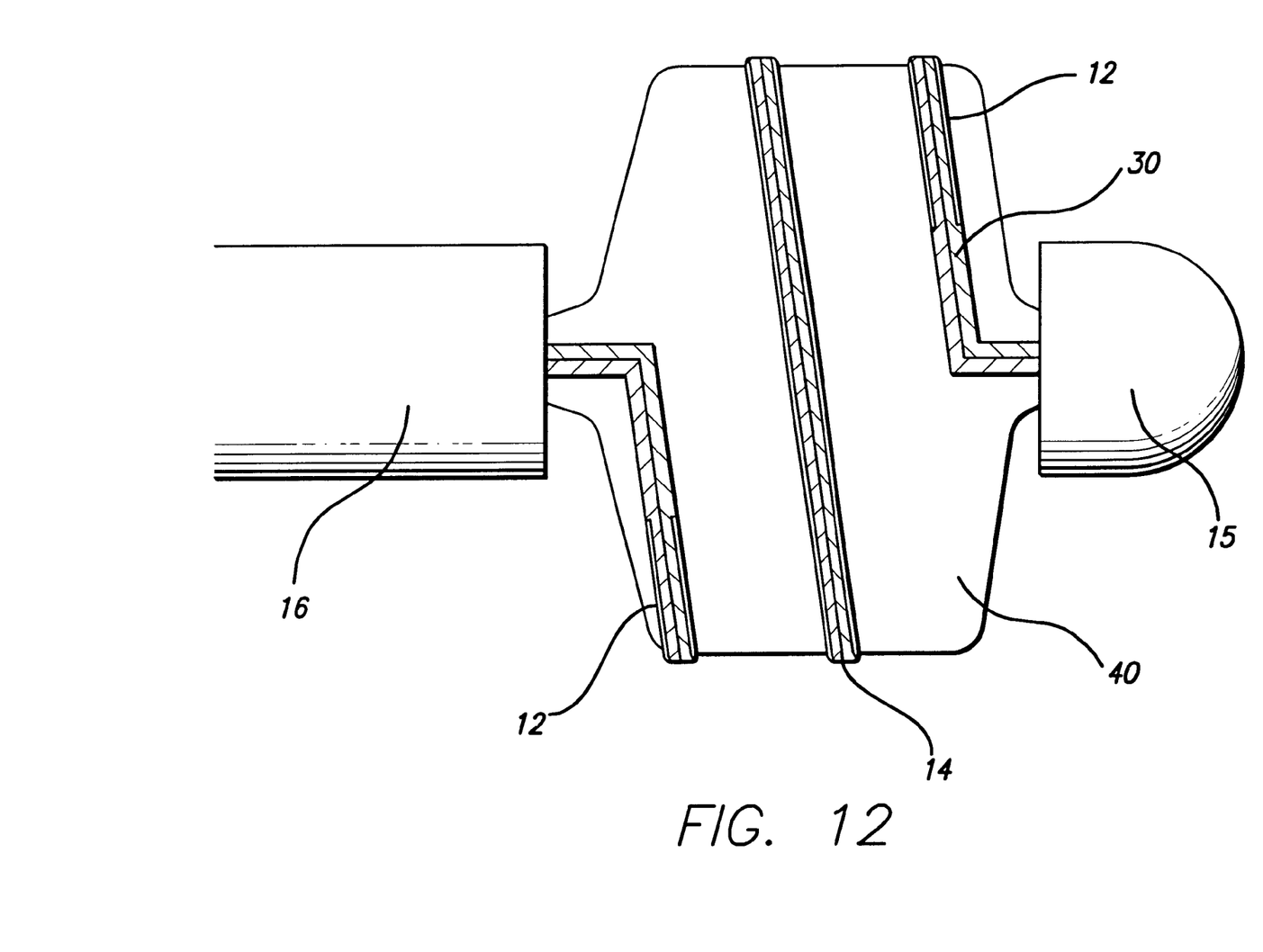
FIG. 12 shows the embodiment of the catheter of FIG. 10 having an inflated balloon in accordance with the invention.

FIGS. 11 and 12 illustrate a catheter 10 with the coil illustrated in FIGS. 9 and 10. The coil 14 is shown in an expanded state. The electrodes 12 preferably occupy only the area of the coil which is to come into apposition with the vein wall during treatment. The balloon 40 formed between the tip 15 and sleeve 16 balloon is shown in a deflated condition in FIG. 11. The balloon can be fabricated from an elastic material, such as silicone rubber or latex, or a noncompliant material. The balloon preferably is inflated using a non-conductive fluid. As illustrated in FIG. 12, the balloon 40 can be inflated after the coil 14 has been expanded away from the catheter 10. The balloon 40 is inflated and comes into contact with the expanded coil 14. The balloon can be used to expand the coil itself without requiring the operator to adjust an actuation mechanism. Where the coil is fabricated from thin nonconductive plastic, such as polyimide, with a plated top section of either intermittent or continuous conductive areas, the balloon 40 supports the otherwise weak plastic stenting. The support provided by the inflated balloon allows for thinner coil strips. For example, a 0.005 inch (0.12 mm) thick polyimide plastic strip can be used to form the coil.

The balloon 40 can ensure proper electrode placement relative to the vein wall while controlling the amount of venous shrinkage. The balloon can be inflated to engage the coil and occlude the vein. As RF energy is applied, the vein becomes heated and begins to shrink. Occluding the blood flow in the vein with the inflated balloon can reduce the effect of blood flow carrying heat away from the treatment site in contact with the electrodes, as well as shielding blood from the heat during treatment to avoid thrombosis formation. Used in conjunction with the previously described external pressure cuff, the vein can be easily and quickly shrunk to a reduced diameter which maintains proper venous function. Alternatively, the balloon can be inflated to define a diameter less than the diameter defined by the expanded coil. During the application of RF energy, the coil 14 is retracted toward the catheter by manipulating the sleeve 16. The diameter defined by the balloon prevents any further retraction of the coil 14 to define the desired reduced diameter for the vein.

The balloon 40 formed between the tip 15 and sleeve 16 can be used in conjunction with or in substitution for the previously described stops and cover. The balloon 40 can be formed in conjunction with the stops, where the stops (not shown) can function as bumpers to prevent damage to the balloon, such as from the bend forming the tangs of the expanding and retracting coil 14.

Figures 13, 14:
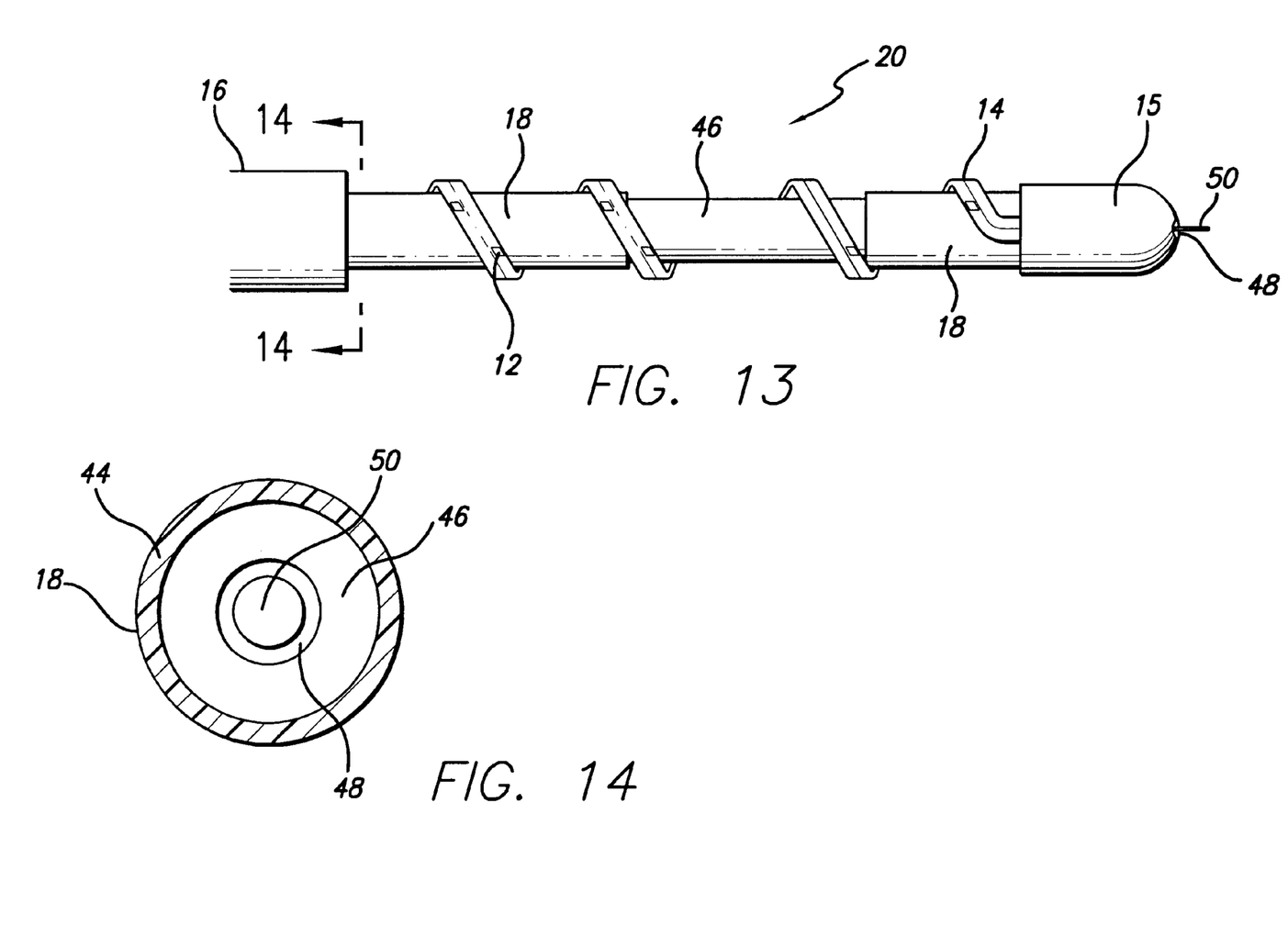
FIG. 13 shows a side view of another embodiment of the catheter having a helical coil in accordance with the invention.
FIG. 14 shows a cross-sectional view of the catheter along lines 14—14 in FIG. 13 illustrating the viscous fluid seal in accordance with the present invention.

Another embodiment of the catheter having a helical coil is illustrated in FIG. 13, and FIG. 14 shows a cross-sectional view of the catheter along lines 14—14 in FIG. 13. As illustrated in FIG. 14, a viscous fluid seal 44 is used between the catheter shaft 46 and the stop 18. The fluid seal may also be found between the catheter shaft 46 and the movable sleeve 16. The fluid seal 44 can accommodate more rotations than an elastomeric cover attached to the sleeve 16 and tip 15. The fluid seal can be a polymerized or unpolymerized silicone, fluorosilicone or urethane gels or oils. One suitable fluid for the fluid seal is silicon oil. For example, five to ten microliters of silicon oil is applied to the moveable interface within the catheter. The viscous fluid remains within the catheter 20 between the catheter shaft 46 and the movable sleeve 16 or stop 18, allows rotational and axial movement of the sleeve, and blocks any wicking or back flow of blood or other body fluids through the catheter. The fluid seal allows the moveable sleeve to be rotated and axially moved along the catheter shaft to expand the electrode coil, and the number of rotations is not limited by the elastomeric limit of a cover attached between the sleeve 16 and tip 15. The fluid seal can be placed anywhere along the interface between the catheter shaft 46 and the sleeve 16 or stop 18, and preferably located before the end of the stop 18 of the sleeve 16.

The catheter illustrated in FIG. 14, further includes a guide wire lumen 48 in the catheter shaft 46. Other lumen for wires or leads for the electrodes are not shown in FIG. 14. The guide wire lumen 48 can accommodate a guide wire 50 to navigate the tortuous venous system. It is to be understood that in embodiments of the catheter for treating smaller veins and other lumen, a guide wire may not be used due to size constraints.

As can be readily ascertained from the disclosure herein, the procedure of the present invention is accomplished without the need for prolonged hospitalization or postoperative recovery. The curative restoration of venous function is possible without the need for continued lifestyle changes, such as frequent leg elevation, the wearing of relatively uncomfortable elastic support stockings or prolonged treatment of recurrent venous stasis ulcers. Moreover, the need for surgical transplantation of veins would not be necessary.

Early treatment of venous disease could prevent more serious complications such as ulceration, thrombophlebitis and thromboembolism. The cost of treatment and complications due to venous disease would be significantly reduced. The need for subsequent treatment and hospitalization would also be reduced from what is currently needed. The medical practitioner can repair or treat several venous sections in a single minimally invasive procedure in a relatively short period of time.

Although the invention has been described in relation to the treatment of the venous system of the lower limbs, it is to be understood that the invention is not limited thereto and may be employed intraluminally to treat hollow anatomical structures in other areas of the body such as hemorrhoids, aneurysms, fallopian tubes, the stomach, esophageal varices, and venous-drainage-impotence of the penis. Furthermore, although the invention has been described as using RF energy from the electrode, it is to be understood that other forms of energy such as microwaves, ultrasound, direct current, and the thermal energy generated from a resistive coil or curie point element may be used as well.

While several particular forms of the invention have been illustrated and described, it will be apparent that various modifications can be made without departing from the spirit and scope of the invention. It is to be understood that the type and dimensions of the catheter and electrodes may be selected according to the size of the vein to be treated. Accordingly, it is not intended that the invention be limited, except as by the appended claims.

What is claimed is:

1. A catheter comprising:
   a catheter body;
   a first strip;
   a second strip;
   a first electrode located on the first strip; and
   a second electrode located on the second strip;
   wherein the first and second strips are connected to the catheter body to form an expandable helical coil, the first and second electrodes remaining a constant distance apart when the coil is being expanded, the first and second strips being electrically conductive, an insulating material partially covering the first and second strips, and the first and second electrodes being formed at exposed portions of the first and second strips.

2. The catheter of claim 1, wherein the first and second strips having sufficient strength to mechanically prevent shrinkage of surrounding tissue heated by the first and second electrodes.

3. The catheter of claim 1, wherein the first and second strips each include a plurality of exposed portions, each exposed portion of the first strip alternates with an exposed portion of the second strip along the path defined by the first strip, and each exposed portion of the second strip alternates with an exposed portion of the first strip along the path defined by the second strip.

4. The catheter of claim 3, wherein the exposed portions of the first strip are spaced equally from one another.

5. The catheter of claim 4, wherein the exposed portions of the second strip are spaced equally from one another.

6. The catheter of claim 5, wherein each exposed portion of the second strip is spaced equally from the two nearest exposed portions of the first strip along the path defined by the first strip.

7. The catheter of claim 1, wherein the first and second electrodes are elongated, and the first electrode is parallel to and has substantially the same length as the second electrode.

8. The catheter of claim 1, further comprising an insulating gap between the first strip and the second strip and a temperature sensor located in the insulating gap.

9. The catheter of claim 8, wherein the temperature sensor is adjacent the first electrode.

10. The catheter of claim 1, wherein the first strip and the second strip are connected together by the insulating material.

11. A catheter comprising:
    a working end having a first segment and a second segment;
    a first conductive band having a first end and a second end, the first end being attached to the first segment, the second end being attached to the second segment, wherein the first conductive band is formed into a coil at the working end;
    a second conductive band located parallel to the first conductive band;
    an insulating gap separating the first conductive band from the second conductive band;
    an insulating material substantially covering the first conductive band and the second conductive band such that a plurality of portions of the first conductive band and the second conductive band remain exposed;
    wherein each exposed portion of the first conductive band alternates with an exposed portion of the second conductive band along a path defined by the first conductive band, and each exposed portion of the second conductive band alternates with an exposed portion of the first conductive band along a path defined by the second conductive band.

12. The catheter of claim 11 wherein the exposed portions of the first conductive band are spaced equally from one another.

13. The catheter of claim 12 wherein the exposed portions of the second conductive band are spaced equally from one another.

14. The catheter of claim 13 wherein the coil defines a substantially cylindrical shape having a cross-sectional diameter, the second segment is constructed to rotate and move toward the first segment, and the cross-sectional diameter of the coil increases as the second segment moves toward the first segment.

15. The catheter of claim 12 wherein the coil defines a substantially cylindrical shape having a cross-sectional diameter, the second segment is constructed to rotate and move toward the first segment, and the cross-sectional diameter of the coil increases as the second segment moves toward the first segment.

16. The catheter of claim 11 wherein the coil defines a substantially cylindrical shape having a cross-sectional diameter, the second segment is constructed to controllably rotate and move toward the first segment, and the cross-sectional diameter increases as the second segment moves toward the first segment.

17. The catheter of claim 11, wherein a seal is located between the first segment and the second segment of the working end.

18. The catheter of claim 11, further comprising a shaft, wherein the second segment surrounds a portion of the shaft, and a fluid seal located between the shaft and the second segment.

19. The catheter of claim 11, wherein a balloon is located between the first segment and the second segment of the working end.

20. The catheter of claim 11, wherein a balloon is located between the working end and the coil.

21. The catheter of claim 11 further comprising at least one temperature sensor in the gap between the first conductive band and the second conductive band.

22. A catheter comprising:
a working end having a first segment and a second segment, the second segment being movable relative to the first segment for a first distance;
a first conductive band having a first end and a second end, the first end being attached to the first segment, the second end being attached to the second segment, wherein the first conductive band is formed into a coil at the working end;
a second conductive band located parallel to the first conductive band;
an insulating gap separating the first conductive band from the second conductive band;
an insulating material partially covering the first conductive band and the second conductive band such that an exposed first portion of the first conductive band and an exposed second portion of the second conductive band are not covered by the insulating material;
wherein the exposed first portion of the first conductive band is parallel to and has substantially the same length as the exposed second portion of the second conductive band.

23. The catheter of claim 22, wherein the coil is expanded by rotating and linearly moving the second segment the first distance towards the first segment.

24. The catheter of claim 22 further comprising a sleeve connected to the second segment, wherein the sleeve is moved over the catheter to controllably move the second segment toward the first segment so that the cross-sectional diameter increases as the second segment moves toward the first segment.

25. The catheter of claim 22, wherein the insulating material covers the first and second bands in order to avoid heating blood within a vein being treated by the catheter.

26. The catheter of claim 22, wherein a seal is located between the first segment and the second segment of the working end.

27. The catheter of claim 22, further comprising a shaft, wherein the second segment surrounds a portion of the shaft, and a fluid seal located between the shaft and the second segment.

28. The catheter of claim 22, wherein a balloon is located between the first segment and the second segment of the working end.

29. The catheter of claim 22, wherein a balloon is located between the working end and the coil.

30. The catheter of claim 22 further comprising at least one thermocouple located in the gap between the first conductive band and the second conductive band.

31. A catheter comprising:
a catheter body having a working end;
a coil having a first end and a second end, the first end and the second end of the coil being connected to the catheter body at the working end, the coil being capable of expanding to define a substantially cylindrical surface area having an effective diameter; and
means for applying energy along the coil wherein the coil having sufficient strength to mechanically prevent shrinkage of surrounding tissue heated by the means for applying energy beyond the effective diameter defined by the coil;
wherein the working end includes a first segment, a second segment constructed to controllably move relative to the first segment, and the effective diameter defined by the coil increases at the working end as the second segment moves toward the first segment.

32. The catheter of claim 31 further comprising a cover located between the first segment and the second segment.

33. The catheter of claim 31 further comprising a shaft, wherein the second segment surrounds a portion of the shaft, and a fluid seal located between the shaft and the second segment.

34. The catheter of claim 31 further comprising a balloon located between the first end and the second end of the coil.

35. The catheter of claim 31 wherein the applying means includes at least two electrodes forming a bipolar pair, and the density of the energy remains uniform along a helical path defined by the coil.

36. The catheter of claim 31 further comprising means for measuring the temperature of venous tissue in contact with the applying means.

37. The catheter of claim 31 wherein the means for applying energy applies energy of uniform density along the coil.

38. A catheter comprising:
a catheter body;
a first strip;
a second strip;
a first electrode located on the first strip; and
a second electrode located on the second strip;
wherein the first and second strips are connected to the catheter body to form an expandable helical coil, the first and second electrodes remaining a constant distance apart when the coil is being expanded, wherein the first electrode is parallel to and has substantially the same length as the second electrode.

39. The catheter in claim 38, wherein the first and second strips are electrically conductive, an insulating material partially covers the first and second strips, and the first and second electrodes are formed at exposed portions of the first and second strips.

40. A The catheter of claim 35, wherein the first strip and the strip are connected together by the insulating material.

41. The catheter of claim 38, further comprising an insulating gap between the first strip and the second strip, and a temperature sensor located in the insulating gap.

42. The catheter of claim 41, wherein the temperature sensor is adjacent the first electrode.

43. A catheter comprising:
a catheter body;
a first strip;
a second strip;
an insulating gap between the first strip and the second strip;
a temperature sensor located in the insulating gap;
a first electrode located on the first strip;
a second electrode located on the second strip; and
wherein the first and second strips are connected to the catheter body to form an expandable helical coil, the first and second electrodes remaining a constant distance apart when the coil is being expanded.

44. The catheter in claim 43, wherein the first and second strips are conductive, an insulating material partially covers the first and second strips, and the first and second electrodes are formed at exposed portions of the first and second strips.

45. The catheter of claim 44, wherein the first and second strips each include a plurality of exposed portions, each exposed portion of the first strip alternates with an exposed portion of the second strip along the path defined by the first strip, and each exposed portion of the second strip alternates with an exposed portion of the first strip along the path defined by the second strip.

46. The catheter of claim 45, wherein the exposed portions of the first strip are spaced equally from one another.

47. The catheter of claim 46, wherein the exposed portions of the second strip are spaced equally from one another.

48. The catheter of claim 47, wherein each exposed portion of the second strip is spaced equally from the two nearest exposed portions of the first strip along the path defined by the first strip.

49. The catheter of claim 44, wherein the first strip and the second strip are connected together by the insulating material.

50. The catheter of claim 43, wherein the first and second electrodes are elongated, and the first electrode is parallel to and has substantially the same length as the second electrode.

51. The catheter of claim 43, wherein the temperature sensor is adjacent the first electrode.

52. The catheter of claim 43, wherein the first and second strips having sufficient strength to mechanically prevent shrinkage of surrounding tissue heated by the first and second electrodes to a selected diameter defined by the first and second strips.

53. A catheter comprising:
a catheter body having a working end;
a coil having a first and a second end connected to the catheter at the working end, the coil being capable of expanding to define a substantially cylindrical surface area having an effective diameter;
means for applying energy along the coil, wherein the coil having sufficient strength to mechanically prevent shrinkage of surrounding tissue heated by the means for applying energy beyond the effective diameter defined by the coil; and
a balloon located between the first end of the coil and the second end of the coil.

54. The catheter of claim 53 wherein the applying means includes at least two electrodes forming a bipolar pair, and the density of the energy remains uniform along a helical path defined by the coil.

55. The catheter of claim 53 further comprising means for measuring the temperature of the tissue in contact with the applying means.

56. The catheter of claim 53, wherein the means for applying energy applies energy of uniform density along the coil.

57. A catheter comprising:
catheter body;
a first strip;
a second strip;
a first electrode located on the first strip;
a second electrode located on the second strip; and
wherein the first and second strips are connected to the catheter body to form an expandable helical coil, the first and second electrodes remaining a constant distance apart when the coil is being expanded, the first and second strips having sufficient strength when expanded to mechanically prevent shrinkage of surrounding tissue heated by the first and second electrodes to a selected diameter defined by the first and second strips.

58. The catheter in claim 57, wherein first electrode is parallel to and has substantially the same length as the second electrode.

59. The catheter in claim 57, wherein the first and second strips are conductive, an insulating material partially covers the first and second strips, and the first and second electrodes are formed at exposed portions of the first and second strips.

60. The catheter of claim 59, wherein each exposed portion of the first strip alternates with an exposed portion of the second strip along the path defined by the first strip, and each exposed portion of the second strip alternates with an exposed portion of the first strip along the path defined by the second strip.

61. The catheter of claim 59, wherein the exposed portions of the first strip are spaced equally from one another.

62. The catheter of claim 59, wherein the exposed portions of the second strip are spaced equally from one another.

63. The catheter of claim 59, wherein each exposed portion of the second strip is spaced equally from the two nearest exposed portions of the first strip along the path defined by the first strip.

64. The catheter of claim 59, wherein the first strip and the second strip are connected together by the insulating material.

* * * * *

UNITED STATES PATENT AND TRADEMARK OFFICE
CERTIFICATE OF CORRECTION

PATENT NO. : 6,322,559 B1
DATED : November 27, 2001
INVENTOR(S) : Jay S. Daulton and Dawn Henderson It is certified that error appears in the above-identified patent and that said Letters Patent is hereby corrected as shown below:

<u>Column 14,</u>
Line 40, change "35", to read -- 39 --.

Signed and Sealed this

Fourteenth Day of May, 2002

Attest:

JAMES E. ROGAN
*Attesting Officer*   *Director of the United States Patent and Trademark Office*